US012678146B2

(12) United States Patent
Sauer

(10) Patent No.: US 12,678,146 B2
(45) Date of Patent: Jul. 14, 2026

(54) DEVICE FOR VESSEL SUPPORT AND HARVESTING

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 503 days.

(21) Appl. No.: 17/634,508

(22) PCT Filed: Aug. 12, 2020

(86) PCT No.: PCT/US2020/045835
§ 371 (c)(1),
(2) Date: Feb. 10, 2022

(87) PCT Pub. No.: WO2021/030380
PCT Pub. Date: Feb. 18, 2021

(65) Prior Publication Data
US 2022/0287696 A1 Sep. 15, 2022

Related U.S. Application Data

(60) Provisional application No. 62/916,581, filed on Oct. 17, 2019, provisional application No. 62/886,772, filed on Aug. 14, 2019.

(51) Int. Cl.
*A61B 17/00* (2006.01)
*A61B 17/04* (2006.01)

(52) U.S. Cl.
CPC .... *A61B 17/00008* (2013.01); *A61B 17/0469* (2013.01); *A61B 2017/00013* (2013.01);
(Continued)

(58) Field of Classification Search
CPC ........ A61B 17/00234; A61B 17/32056; A61B 2017/00358; A61B 17/0485; A61B 17/12;
(Continued)

(56) References Cited

U.S. PATENT DOCUMENTS 3,835,854 A * 9/1974 Jewett ................ A61M 25/0113
604/159
9,730,572 B2 8/2017 Hasser et al.
(Continued)

OTHER PUBLICATIONS

International Search Report and Written Opinion for International Application No. PCT/US2020/45835, mailed Nov. 4, 2020.
(Continued)

*Primary Examiner* — Kankindi Rwego
(74) *Attorney, Agent, or Firm* — Michael E. Coyne

(57) ABSTRACT

Another surgical device is also disclosed. The surgical device includes a flexible distal tip, which may also include a distal opening, a shaft interface opening on a proximal end of the flexible distal tip, an intermediate opening located between the distal opening and the shaft interface opening, and a channel coupling the shaft interface opening and the intermediate opening. The device may also include a hollow shaft connected to the shaft interface opening, a handle coupled to the hollow shaft, a suture locking device slidable within the handle, and a sliding actuator coupled to the hollow shaft.

9 Claims, 14 Drawing Sheets

(52) U.S. Cl.
CPC ............... *A61B 2017/00358* (2013.01); *A61B 2017/00367* (2013.01); *A61B 2017/0042* (2013.01); *A61B 2017/00969* (2013.01)

(58) Field of Classification Search
CPC ........ A61B 17/12009; A61B 17/00008; A61B 17/0469; A61B 2017/00367; A61B 2017/0042; A61B 2017/0036; A61B 2017/00424; A61B 2017/0046; A61M 25/0113
USPC ......................................................... 606/139
See application file for complete search history.

(56)                    References Cited

U.S. PATENT DOCUMENTS

| | | | |
|---|---|---|---|
| 10,300,250 B2 | 5/2019 | Erpen | |
| 10,349,966 B2 | 7/2019 | Thapliyal et al. | |
| 2005/0283171 A1* | 12/2005 | Bellafiore | ........ A61B 17/06109 |
| | | | 606/144 |
| 2009/0157076 A1* | 6/2009 | Athas | ................. A61B 18/1477 |
| | | | 606/41 |
| 2011/0245850 A1 | 10/2011 | Van Der Burg et al. | |
| 2011/0301622 A1* | 12/2011 | Oren | .................. A61B 17/0483 |
| | | | 606/145 |
| 2015/0142041 A1* | 5/2015 | Kendale | ............... A61B 1/0125 |
| | | | 606/190 |
| 2015/0313452 A1* | 11/2015 | Hasser | ................... A61B 34/35 |
| | | | 600/102 |
| 2017/0027597 A1 | 2/2017 | Walen | |
| 2018/0271554 A1* | 9/2018 | Thapliyal | ............... A61N 7/022 |

OTHER PUBLICATIONS

EP Search Report, dated Aug. 25, 2023, Application No 20852712. 7, corresponding to PCT/US2020045835, 7 pages.

* cited by examiner

36

40

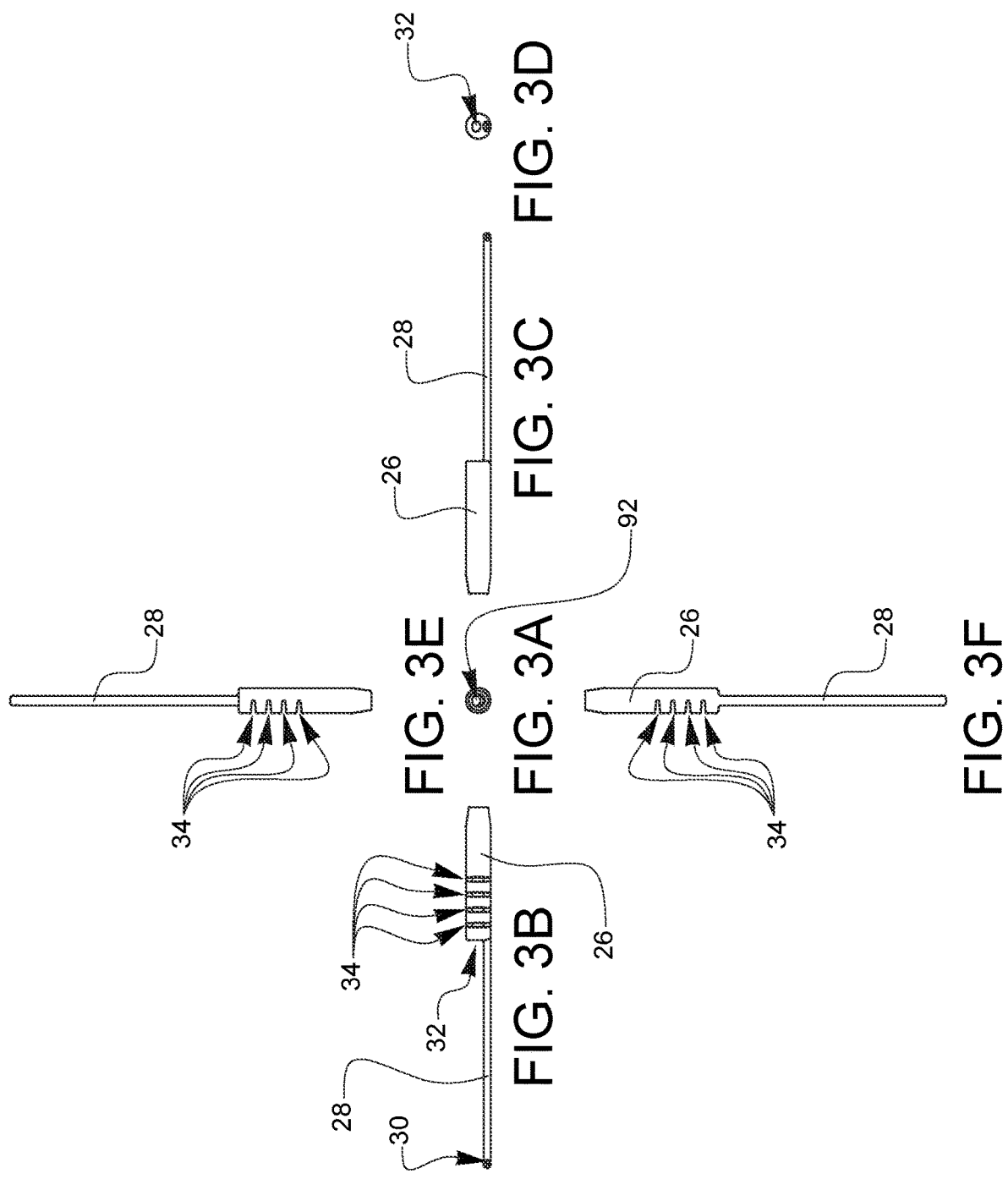

DEVICE FOR VESSEL SUPPORT AND HARVESTING

REFERENCE TO RELATED APPLICATIONS

This patent application is a national stage application, filed under 35 U.S.C. § 371, of International Patent Application No. PCT/US20/45835, filed on Aug. 12, 2020, which claims priority to U.S. Provisional Patent Application No. 62/886,772, filed Aug. 14, 2019, and U.S. Provisional Patent Application No. 62/916,581, filed Oct. 17, 2019, each of which is incorporated by reference herein in its entirety.

FIELD

The claimed invention relates to minimally invasive surgical devices, and more specifically to a surgical device used in minimally invasive surgical procedures.

BACKGROUND

Minimally invasive surgical approaches are gaining increased interest in relation to coronary procedures. Coronary revascularization procedures such as the grafting of the internal thoracic artery (ITA) has shown superior long-term patency and improved patient outcome in coronary artery bypass graft (CABG) surgeries. While conventional approaches to ITA harvesting have included median sternotomy or multiple thoracoports, a minimally invasive approach is desirable. A minimally invasive procedure related to revascularization using either the left or right internal thoracic artery (ITA), or the left or right internal mammary artery (IMA) may utilize access to the ITAs via sub-xiphoid access, where increased surgical space is gained by accessing the internal thoracic arteries via incision at the subxiphocostal region.

Upon harvesting either the left internal thoracic artery (LITA) or the right internal thoracic artery (RITA) anastomoses to the left anterior descending (LAD) coronary artery and to the right coronary artery (RCA), respectively, can be performed without cardiopulmonary bypass (CPB). A significant advantage of this approach is that a perfectly harvested ITA graft can be perfectly anastomosed to the usual site on the LAD artery, or onto the RCA artery. A minimally invasive ITA harvesting procedure involving sub-xiphoid access also results in superior cosmetic results, is reasonably painless, and the arterial grafting can be accomplished on the beating heart. Recent approaches of minimally invasive ITA harvesting surgical techniques have been shown to result in increased effective length of ITA bypasses, reduced operation times, and improved patient recovery.

While less invasive surgical approaches for ITA harvesting and CABG have shown promise, the visualization, maintenance of insufflation, and distal suturing of a coronary anastomosis in totally endoscopic coronary artery bypass grafting on the beating heart is technically demanding. Likewise, a minimally invasive surgical approach should not compromise the reliability of a cardiac repair. Therefore, there is a need for suitable surgical tools to aid in the take-down or harvesting of ITA during minimally invasive harvesting and revascularization surgical procedures.

BRIEF DESCRIPTION OF THE DRAWINGS

FIGS. 3A, 3B, 3C, 3D, 3E, and 3F are front, left side, right side, rear, top, and bottom elevational views, respectively of a flexible distal tip of FIG. 1.

Figure 1:
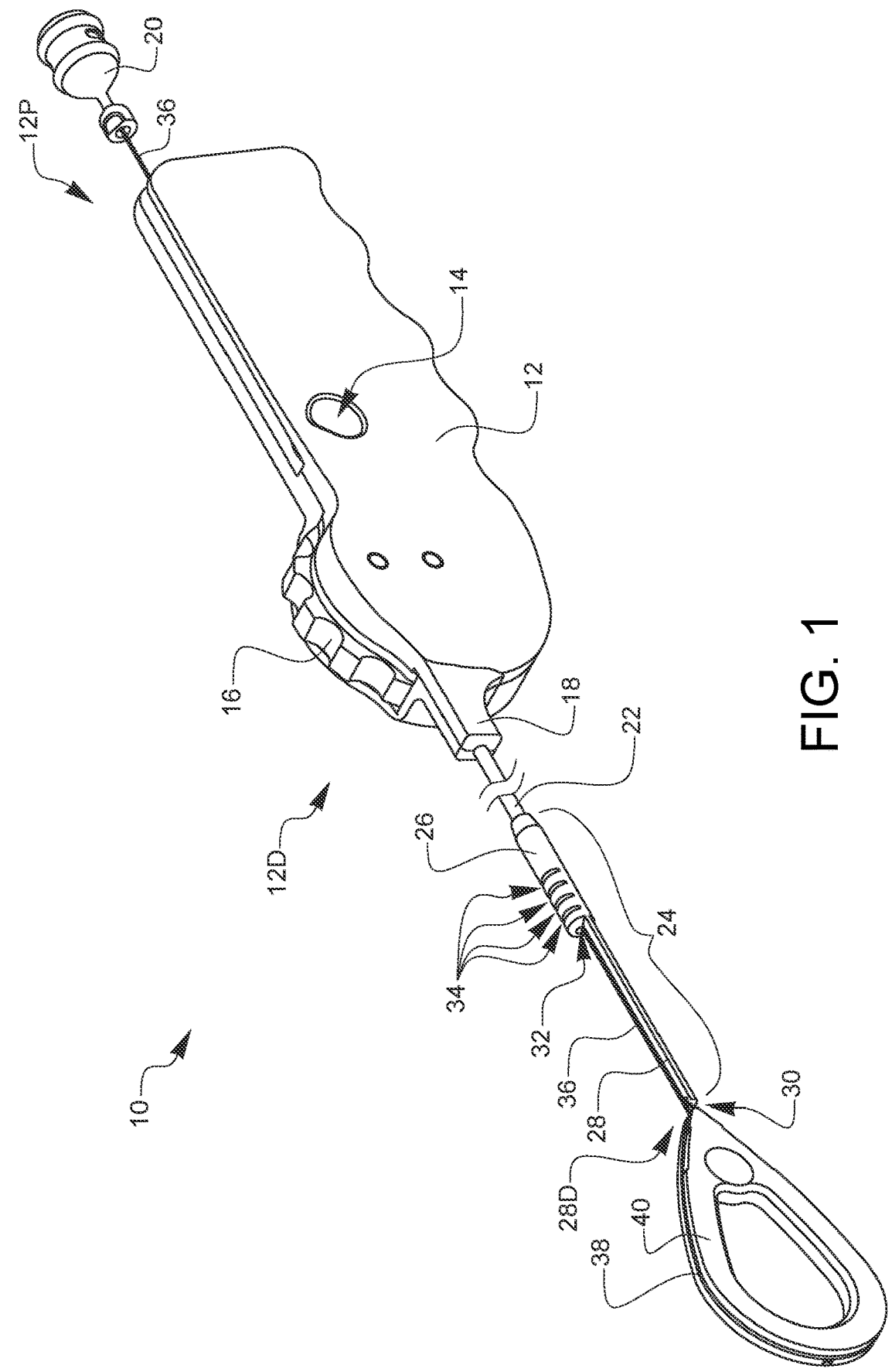
FIG. 1 is a top-left-front perspective view of one embodiment of a minimally invasive surgical device.

It will be appreciated that for purposes of clarity and where deemed appropriate, reference numerals have been repeated in the figures to indicate corresponding features, and that the various elements in the drawings have not necessarily been drawn to scale in order to better show the features.

SUMMARY

A surgical device is disclosed. The surgical device includes a flexible distal tip, which may further include a distal opening, a shaft interface opening on a proximal end of the flexible distal tip, an intermediate opening located between the distal opening and the shaft interface opening; and a channel coupling the shaft interface opening and the intermediate opening. The surgical device may also include a hollow shaft connected to the shaft interface opening and an actuator coupled to the hollow shaft.

Another surgical device is also disclosed. The surgical device includes a flexible distal tip, which may also include a distal opening, a shaft interface opening on a proximal end of the flexible distal tip, an intermediate opening located between the distal opening and the shaft interface opening, and a channel coupling the shaft interface opening and the intermediate opening. The device may also include a hollow shaft connected to the shaft interface opening, a handle coupled to the hollow shaft, a suture locking device slidable within the handle, and a sliding actuator coupled to the hollow shaft.

DETAILED DESCRIPTION

FIG. 1 is a top-left-front perspective view of one embodiment of a minimally invasive surgical device. FIG. 1 shows a minimally invasive surgical device 10, having a housing 12, the housing 12 defining an opening or window 14, an actuator dial 16 enclosed therein, and a housing coupler 18 at the distal end 12D of the housing 12. The purpose and operation of the actuator dial 16 will be discussed later, although alternate embodiments could have alternate means or structure used in actuation. Connected to the housing coupler 18 is a hollow shaft 22. Inserted within the hollow shaft 22 is a flexible lumen or tube, not shown in this view. At the opposite end of the shaft 22 is a flexible distal tip 24 which defines a distal tip body 26 and a flexible loop portion 28. The flexible loop portion 28 has a distal opening 30 at its proximal end 28D. The distal tip body 26 also has several flexure voids 34 and an intermediate opening 32, which is in communication with the inside of the lumen or tube held within the hollow shaft 22. The flexure voids 34 allow the distal tip body 26 to flex, bend and provide more flexibility to the flexible distal tip 24 overall. The addition of one or more flexure voids 34 provides relief space in the distal tip body 26 of the flexible distal tip 24 such that when the distal tip body 26 is flexed, it is met with less resistance by the overall structure of the distal tip body 26. Exiting from the intermediate opening 32 of the flexible distal tip 24 is a snare wire 36 which forms a snare wire loop 38 at the distal end 28D of the flexible loop portion 28 of the flexible distal tip 24. The snare wire loop 38 is temporarily fortified by being held within and encircling a target 40. Exiting from the proximal end 12P of the housing 12 is another end of the snare wire 36 which has a metal pull tab 20 crimped onto the end of the snare wire 36. The metal pull tab 20, also referred to as a chalice because of the shape is shown in this embodiment, but other embodiments may have similar pull tabs made from plastic, rubber, or other materials. Still other embodiments may have metal curved handles or other means of grasping the end of the snare wire 36.

Figure 2A:
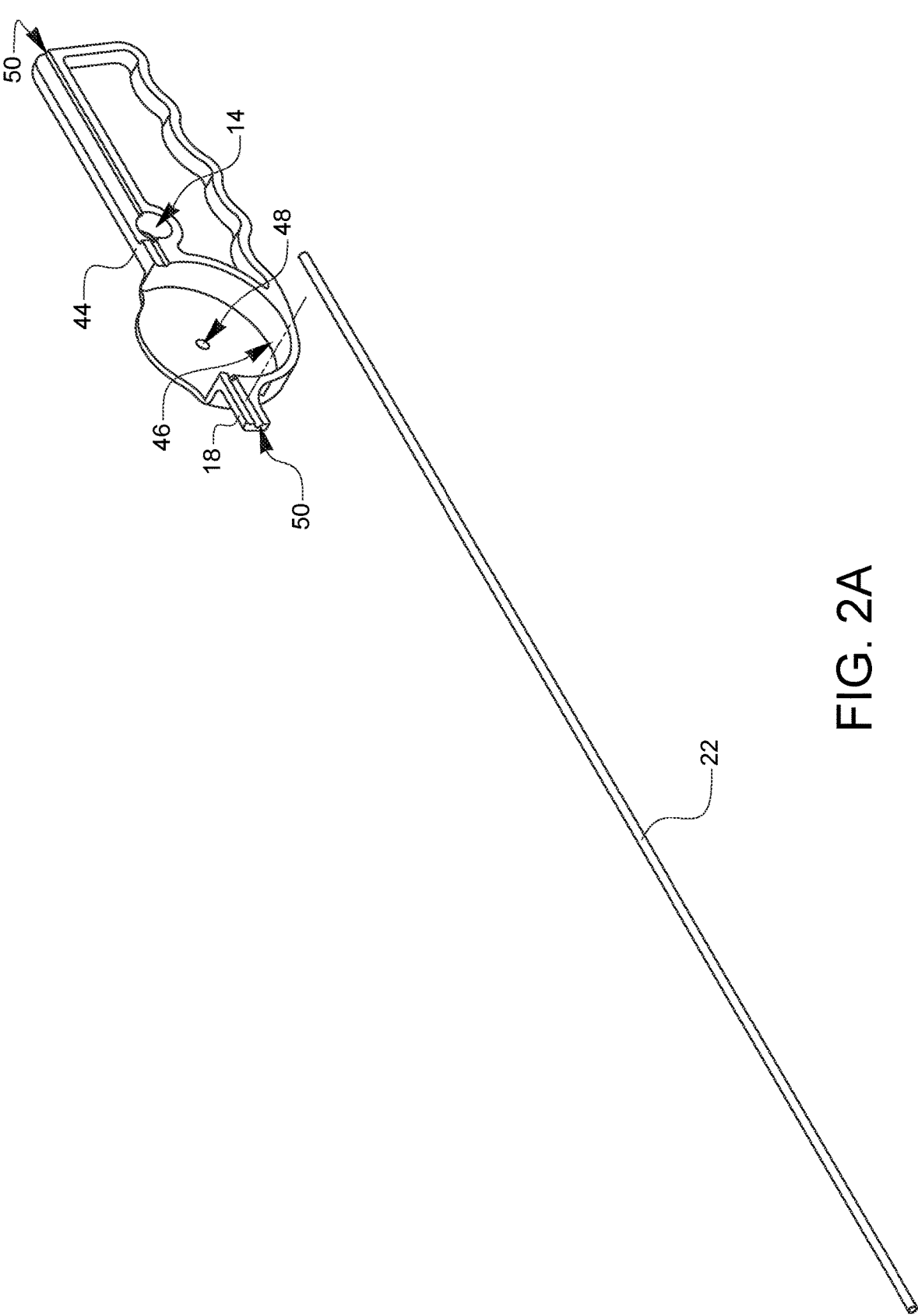
FIG. 2A-2E are a series of exploded views illustrating the assembly steps of the minimally invasive surgical device of FIG. 1.
Figure 2B:
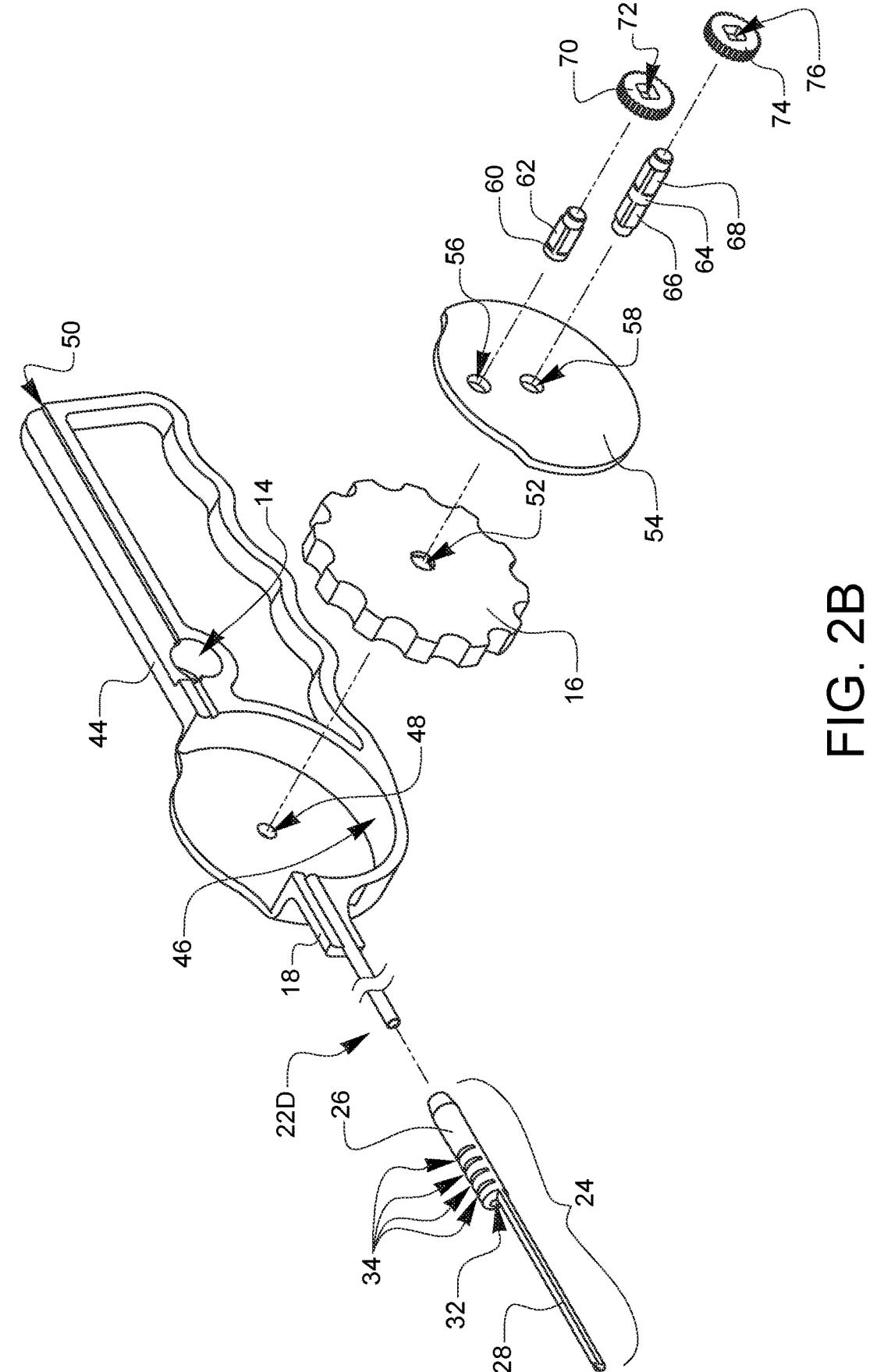
Figure 2C:

FIG. 2A-2E are a series of exploded views illustrating the assembly steps of the minimally invasive surgical device of FIG. 1. FIG. 2A is an exploded view illustrating the initial assembly steps of the minimally invasive surgical device of FIG. 1. A first housing half 44 having a hole 48 forms part of the minimally invasive surgical device of FIG. 1. The first housing half 44 also defines a portion of the window 14, a portion of a recess 46, part of the coupler 18, and a channel 50 which will communicate from the distal end 12D to the proximal end 12P of the housing 12. The hollow shaft 22 is inserted and fixedly attached to the first housing half 44 in the channel 50 in the housing coupler 18 portion. In FIG. 2B, the actuator dial 16, defining a hole 52 is placed within the recess 46 portion of the first housing half 44. Next, a bearing plate 54 having a central hole 58 and a hole 56 is placed within the recess 46. The central hole 58 in the bearing plate 54 aligns with the hole 52 in the actuator dial 16, and the hole 48 on the first housing half 44. A first axle 60 having a keyed portion 62 is placed into hole 56, and a second axle 64 having a first keyed portion 66 and a second keyed portion 68 is placed into central hole 58 in bearing plate 54, into hole 52 in actuator dial 16, and finally into hole 48 in the first housing half 44. A first toothed roller 70 having a keyed hole 72 is placed over the keyed portion 62 of the first axle 60, and a second toothed roller 74 having a keyed hole 76 is placed over the second keyed portion 68 of second axle 64. The flexible distal tip 24 is fixedly attached onto a distal end 22D of the hollow shaft 22. It should be noted that once the flexible distal tip 24 is attached to the hollow shaft 22, the intermediate opening 32 on the flexible distal tip 24 remains in communication with the channel 50 in the housing 12 of the minimally invasive surgical device 10. FIG. 2C illustrates the snare wire 36 being placed over the target 40. While not shown in this series, the snare wire 36 is subsequently wound around the target 40 to form a snare wire loop 38 around the target 40, the details of which is well known to those skilled in the arts.

Figure 2D:
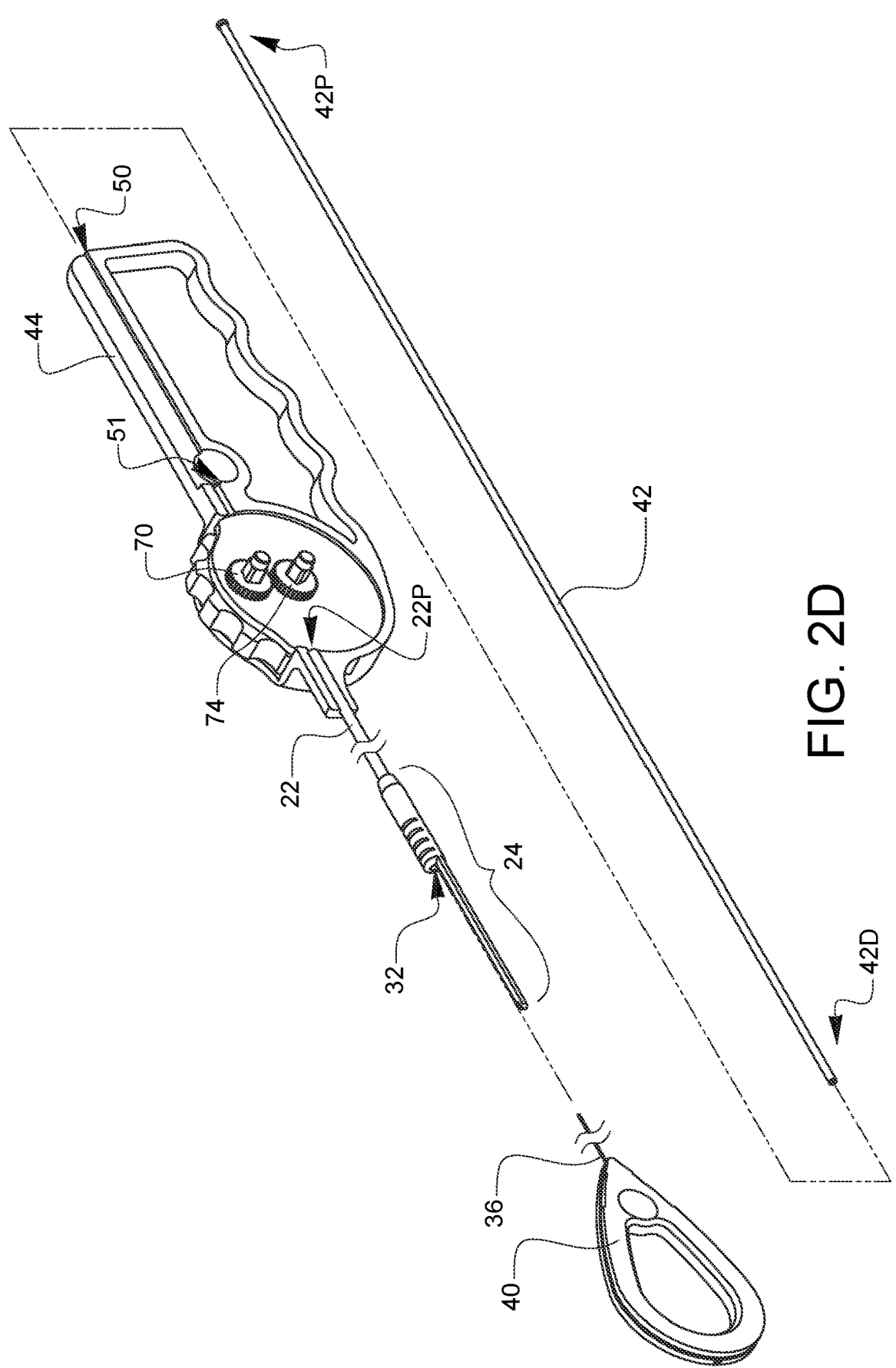
Figure 2E:
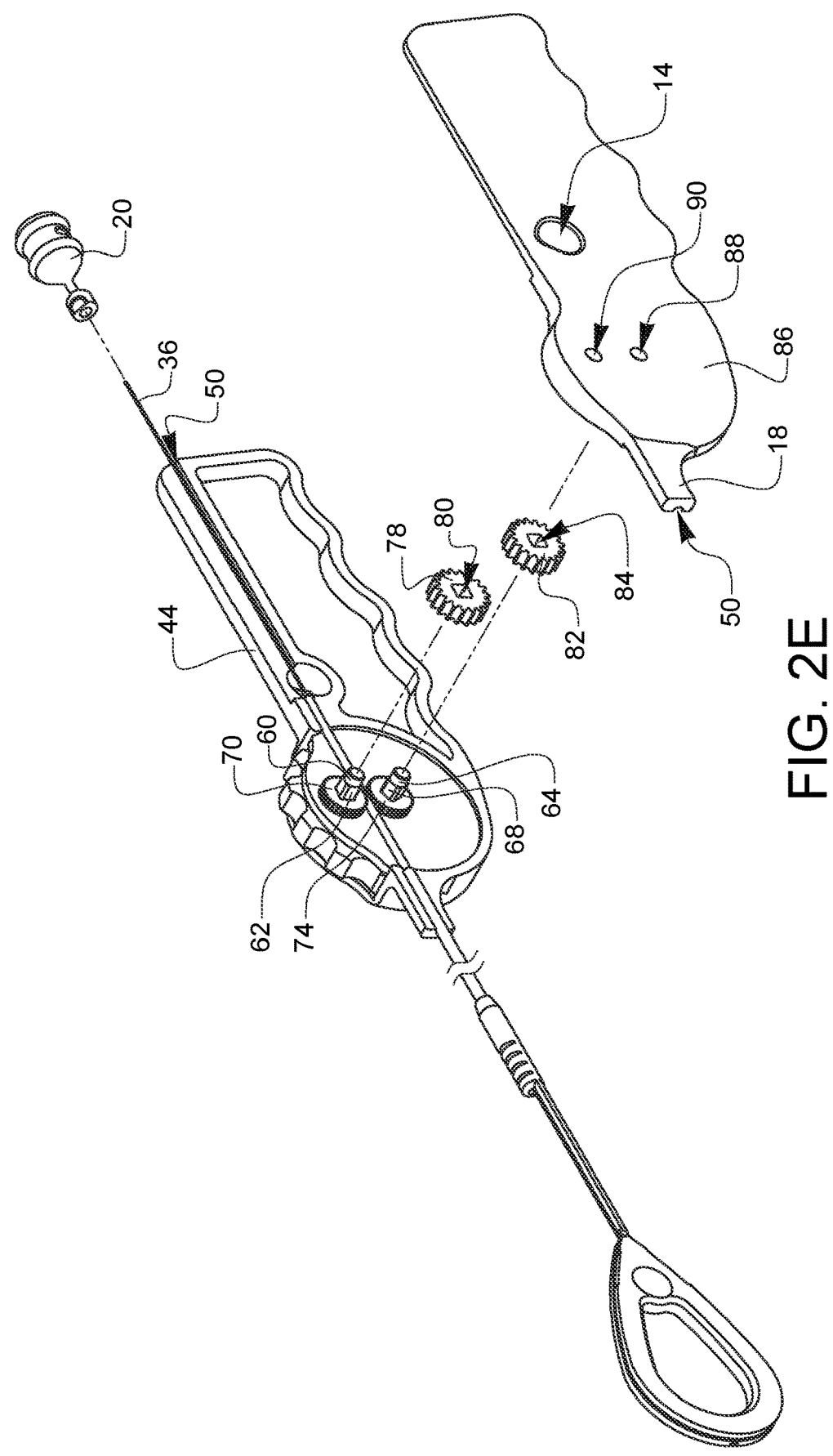

FIG. 2D shows the insertion of a lumen 42 into the channel 50 of the first housing half 44, by way of inserting the distal end 42D of the lumen 42 into the channel 50 and then into the proximal end 22P of the hollow shaft 22. The distal end 42D of the lumen 42 is flared, and therefore cannot be inserted past a stop 51 defined by the first housing half 44. At this point, lumen 42 is held between first toothed roller 70 and second toothed roller 74, and will move as the first toothed roller 70 and the second toothed roller 74 are rotated by the actuation of actuator dial 16. FIG. 2E illustrates the final assembly steps of the minimally invasive surgical device, continuing with a metal pull tab 20 being crimped on the end of the snare wire 36 protruding from the exit of the channel 50. Next, a first gear 78 having a keyed hole 80 are placed over the keyed portion 62 of the first axle 60 and a second gear 82 having a keyed hole 84 is placed over the second keyed portion 68 of second axle 64. Finally, a second housing half 86 is fixedly attached to the first housing half 44, completing the assembly.

FIGS. 3A, 3B, 3C, 3D, 3E, and 3F are front, left side, right side, rear, top, and bottom elevational views, respectively of a flexible distal tip of FIG. 1. The locations and orientation of previously described features of the flexible distal tip 24 are shown in these figures, such as the distal tip body 26, the flexure voids 34, the intermediate opening 32, the flexible loop portion 28, and the distal opening 30 on the flexible loop portion 28. Also shown is the location of the shaft interface opening 92. The distal tip body 26 portion of the flexible distal tip 24 defines the shaft interface opening 92. The shaft interface opening 92 is configured to allow a passthrough or channel (not visible in this view) from the shaft interface opening 92 to the intermediate opening 32 for passing suture or snare or other filaments through the flexible distal tip 24 and into the hollow shaft 22 and lumen 42, which are not shown in this view. This configuration and theory of operation will be discussed in regard to subsequent figures.

Figure 4A:
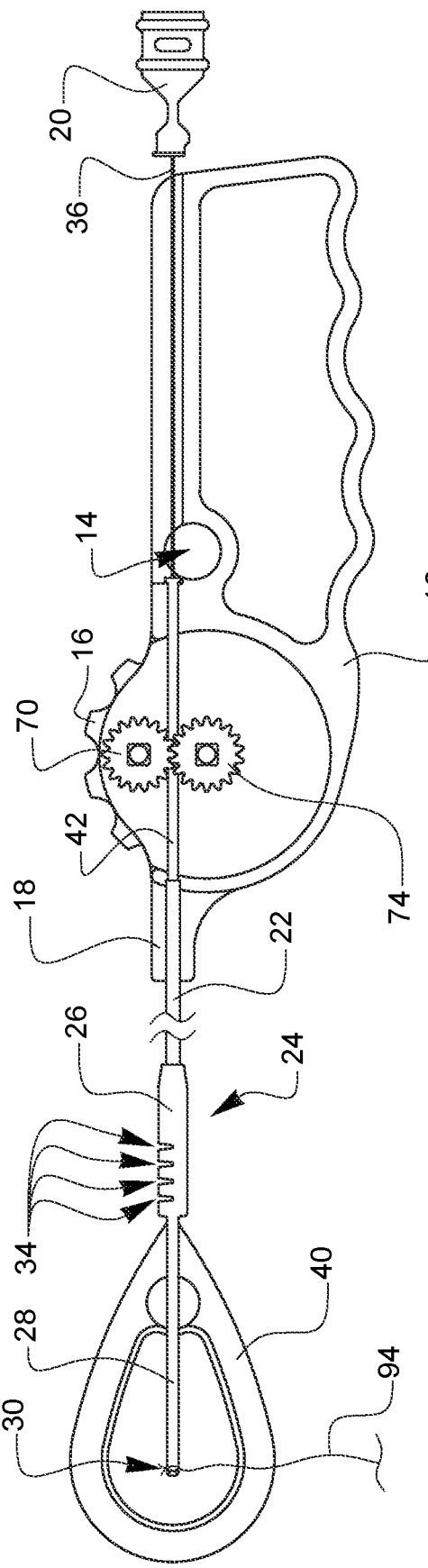
FIGS. 4A-4E are side partial cross-sectional views of the minimally invasive surgical device of FIG. 1, illustrating the operational principles of the minimally invasive surgical device.
Figure 4B:
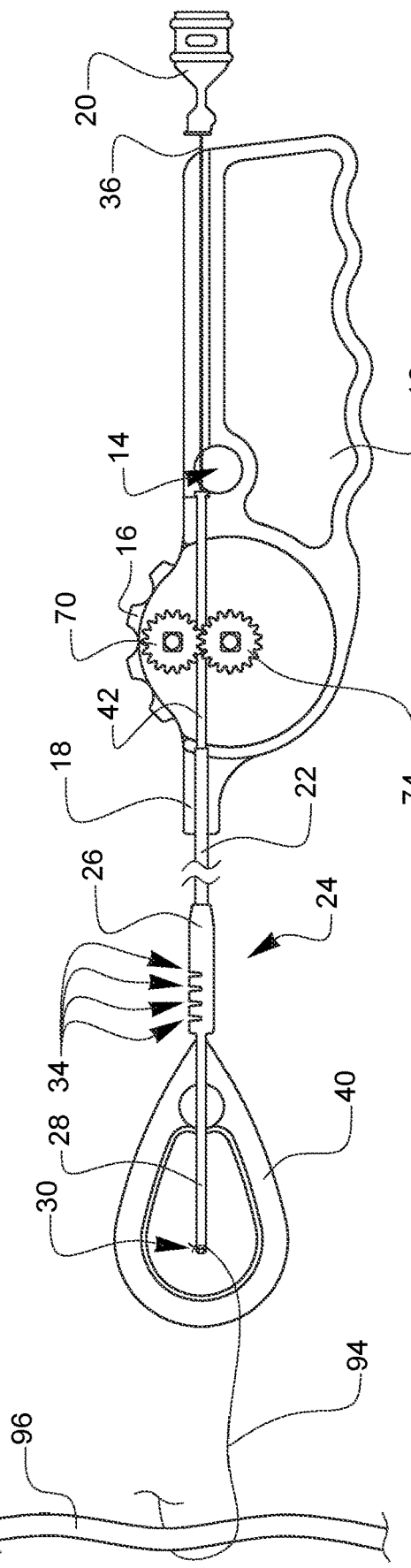
Figure 4C:
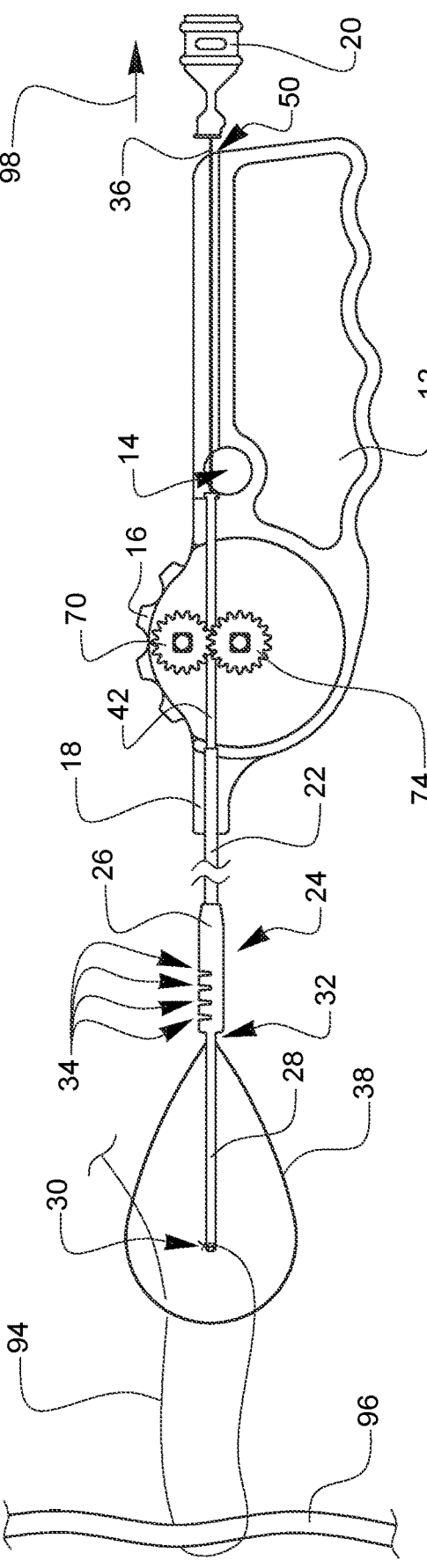
Figure 4D:
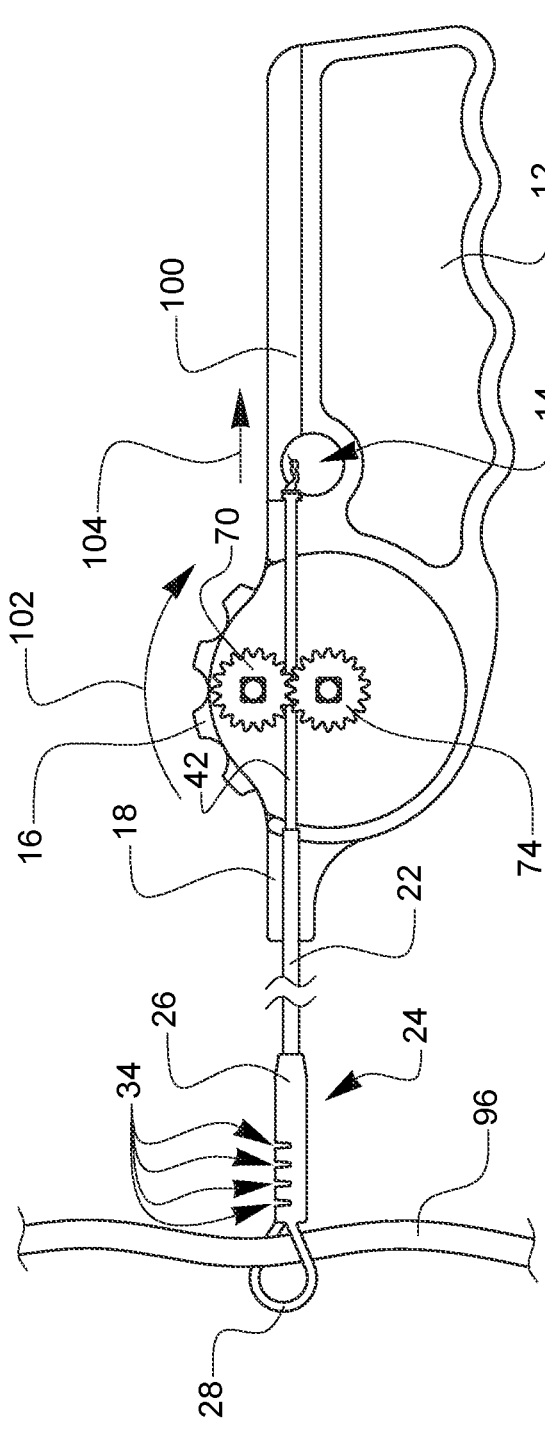
Figure 4E:
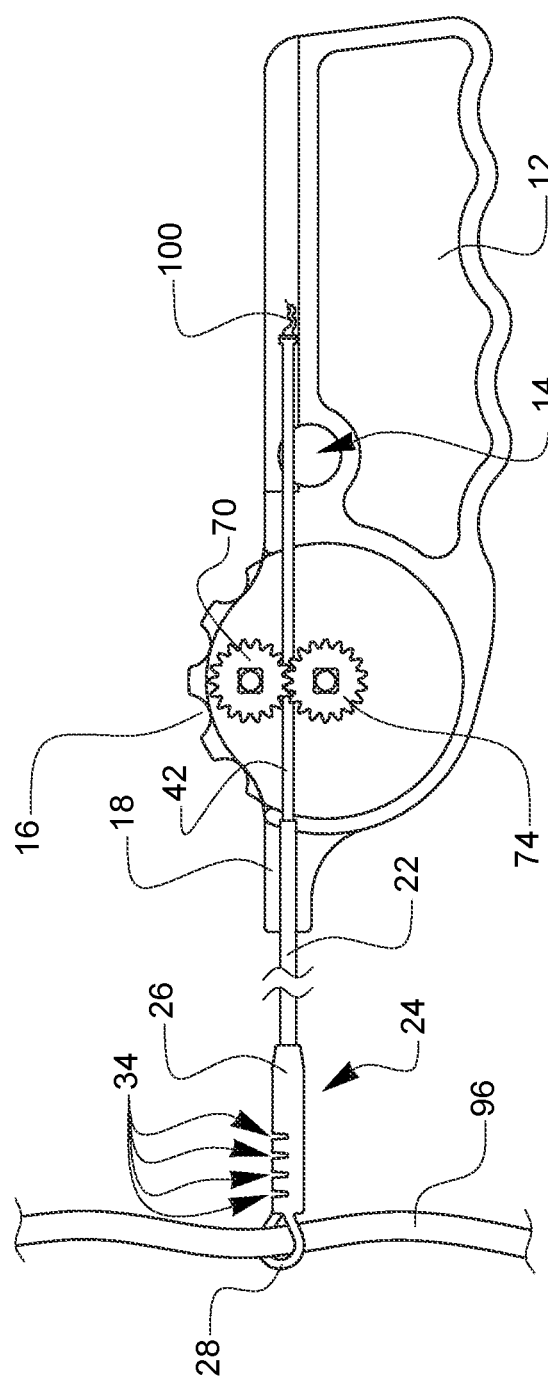

FIGS. 4A-4E are side partial cross-sectional views of the minimally invasive surgical device of FIG. 1, illustrating the operational principles of the minimally invasive surgical device. FIG. 4A shows a side view of the minimally invasive surgical device 10 of FIG. 1, with a suture 94 threaded through and tied to the distal opening 30 of the flexible loop portion 28 of flexible distal tip 24. Other means of attaching suture or other filament known to those skilled in the art may be used to fasten a suture to the distal opening 30 of the flexible loop portion 28. A vessel 96 is illustrated in FIG. 4B, shown without surrounding tissue or other anatomical features for the purpose of clarity. The suture 94 is shown wrapped around the vessel 96. This can be accomplished with the use of graspers or other suitable surgical tools. FIG. 4C shows the target 40 removed from the snare wire loop 38 and the suture 94 passed through the snare wire loop 38. Next, the metal pull tab 20 attached to the snare wire 36 is pulled in direction 98, which snares or pulls the end of the suture 94 captured in the snare wire loop 38 past the flexible loop portion 28 and into the intermediate opening 32 of the flexible distal tip 24, through the inside of the lumen 42 which is held inside the hollow shaft 22 and out through the channel 50 of the housing 12. Once the snare 36 is pulled completely in direction 98, a mechanical fastener 100 is crimped onto the suture 94, as shown in FIG. 4D. Access to apply the mechanical fastener 100 is gained through the window 14 in the housing 12. At this point the suture 94 attached to the distal opening 30 of the flexible loop portion 28 has formed a flexible loop around the vessel 96. Turning the actuator dial 16 in direction 102 turns both the first toothed roller 70 and the second toothed roller 74, which grips lumen 42 and pushes lumen 42 in direction 104. FIG. 4E shows the state of the minimally invasive surgical device 10 after actuator dial 16 has been turned in direction 102. It should be noted that the lumen 42 has moved such that the mechanical fastener 100 is no longer aligned with window 14, and the loop formed by the flexible loop portion 28 on the flexible distal tip 24 is smaller and provides a tighter grip on vessel 96 if desired by the surgeon during a minimally invasive surgical procedure. The adjustment of actuator dial 16 in either direction will move lumen 42 back and forth inside the housing 12, and therefore make the loop formed by the flexible loop portion 28 of the flexible distal tip 24 looser or tighter on a targeted vessel 96 thus effectively supporting a vessel during a minimally invasive surgical procedure, such as vessel harvesting. It should be noted that other means of fastening suture or filament to the device and alternate embodiments described herein may be employed.

Figure 5A:
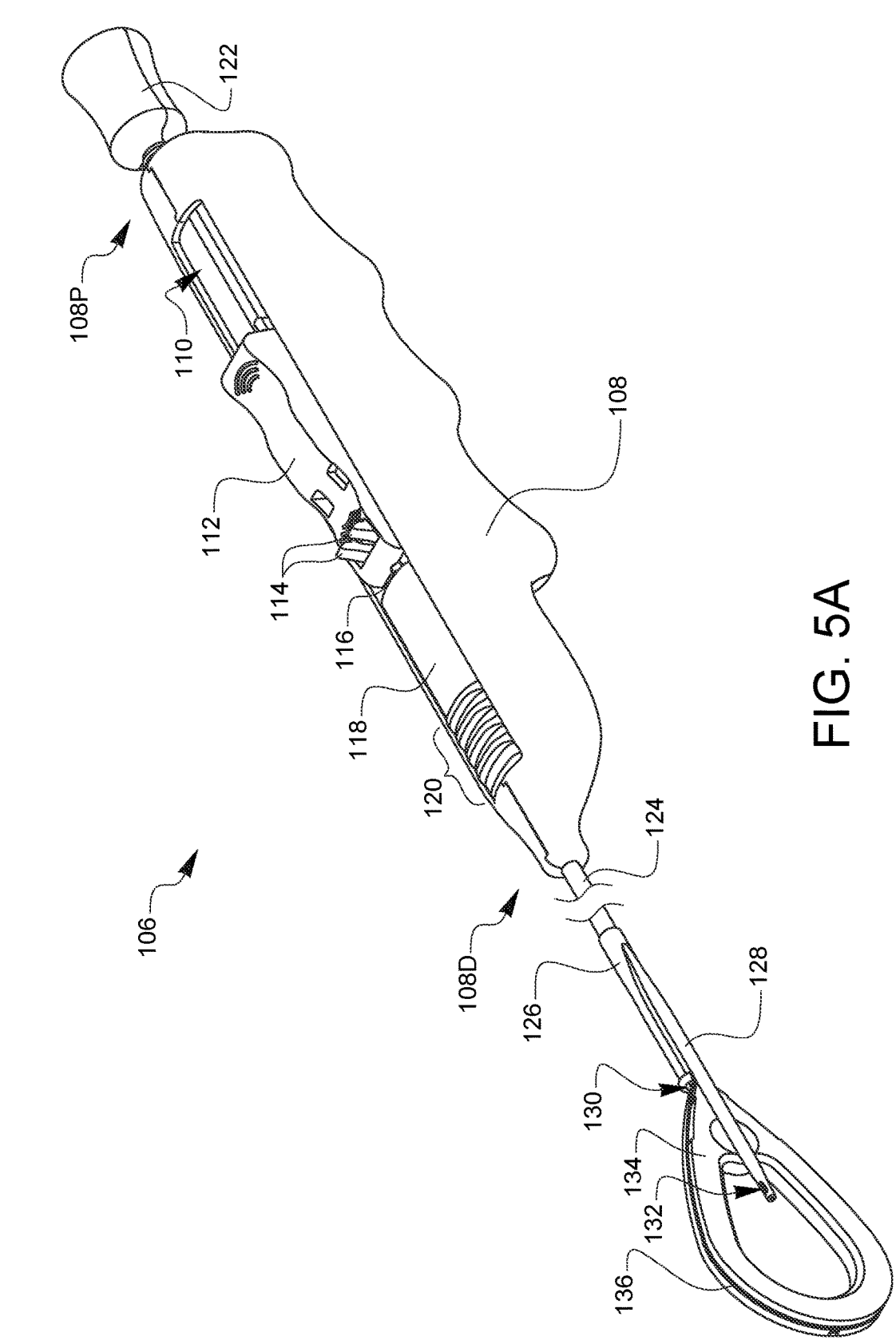
FIGS. 5A-5B are top-left-front perspective views of another embodiment of a minimally invasive surgical device.
Figure 5B:
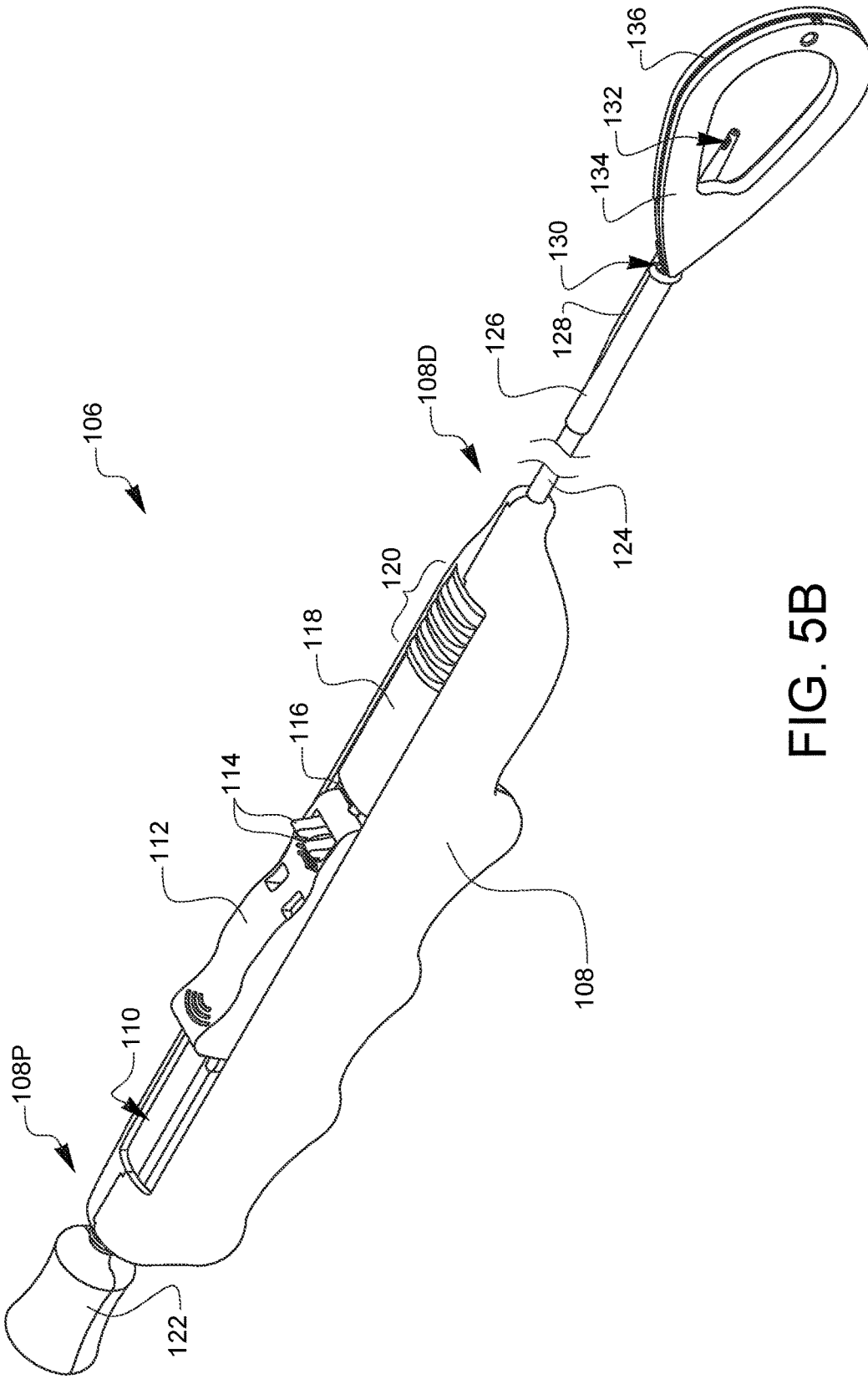

FIGS. 5A-5B are top-left-front perspective views of another embodiment of a minimally invasive surgical device. FIG. 5A shows a minimally invasive surgical device 106, having a housing 108, the housing 108 defining a channel 110. The channel 110 is a recess positioned longitudinally along the housing 108 configured to hold a suture locking device 112 and an actuator slider 118 and allow the longitudinal movement of the suture locking device 112 and the actuator slider 118 along the channel 110 from a distal end 108D to a proximal end 108P of the minimally invasive surgical device 106. The suture locking device 112 has several latch elements 114 and a tube 116 connected to the suture locking device 112. A hollow shaft 124 is connected to the distal end 108D of the housing 108. Connected to the shaft 124 is a distal tip body 126 which defines a flexible loop portion 128. The distal tip body 126 further defines a distal tip body opening 130 and the flexible loop portion 128 further defines a distal opening aperture 132. The distal tip body opening 130 is in communication with the inside of the tube 116 held within the hollow shaft 124. Exiting from the distal tip body opening 130 of the distal tip body 126 is a snare wire which forms a snare wire loop 136 at the distal end of the distal tip body 126. The snare wire loop 136 is temporarily fortified by being held within and encircling a target 134. Exiting from the proximal end 108P of the housing 108 is another end of the snare wire which has a pull tab 122 crimped onto the end of the snare wire. Other embodiments of the pull tab 122 may have similar pull tabs made from plastic, rubber, or other materials. Still other embodiments may have metal curved handles or other means of grasping the end of the snare wire.

Various advantages of a device for vessel harvesting have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical device, comprising:

a housing, an elongated shaft coupled to a first portion of the housing, the shaft extending from a proximal end to a distal end along a shaft axis, the shaft having one or more interior surfaces defining an interior portion;

a flexible distal tip assembly comprising:

a distal tip body that extends along a body axis from a proximal end to a distal end, wherein the proximal end of the distal tip body is coupled to the distal end of the shaft, the distal tip body having one or more interior surfaces defining an interior portion that is in communication with the interior portion of the shaft;

a flexible loop portion that extends along a loop axis from a proximal end to a distal end, wherein the proximal end of the flexible loop portion is disposed at the distal end of the distal tip body, wherein the flexible loop portion is displaceable between a first position, in which the loop axis is linear and aligned with the body axis, and a second position, in which the distal end of the flexible loop portion is disposed at or adjacent to the proximal end of the flexible loop portion; and an actuator mechanism coupled to the housing, the actuator mechanism comprising:

a first roller rotatably coupled to a second portion of the housing, a second roller rotatably coupled to a third portion of the housing, an actuator dial coupled to a fourth portion of the housing, the actuator dial coupled to the first roller such that a rotation of the actuator dial in a first rotational direction rotates the first roller in the first rotational direction, and when the actuator dial is rotated in the first rotational direction, the first roller is configured to displace a lumen disposed between the first roller and the second roller in a first linear direction, wherein a first portion of the lumen is configured to be disposed within the interior portion of the shaft such that the lumen is configured to displace in the first linear direction within the interior portion of the shaft, and wherein a first portion of a suture is configured to be coupled to the distal end of the flexible loop portion and a second portion of the suture is configured to extend through an interior portion of the lumen such that:

(a) when the suture is in a first unsecured state, a third portion of the suture extends from the proximal end of the lumen and the third portion of the suture is configured to be displaced away from the proximal end of the lumen such that the distal end of the flexible loop portion is displaced from the first position to the second position in which the flexible loop portion is configured to surround a vessel to form a first loop state around the vessel, and (b) when the suture is in a second secured state, a fourth portion of the suture that extends from the proximal end of the lumen when the flexible loop portion is in the second position is secured so as to not be displaceable relative to the proximal end of the lumen and such that when the lumen is displaced in the first linear direction, the distal end of the flexible loop portion is displaced to or proximally beyond the proximal end of the distal tip body to a third position in which the flexible loop portion is configured to form a second loop state around the vessel that is tighter than the first loop state.

2. The surgical device of claim 1, wherein the distal tip body further comprises a flexure void.

3. The surgical device of claim 1, wherein an axis of rotation of the first roller is normal to the shaft axis, and an axis of rotation of the second roller is normal to the shaft axis.

4. The surgical device of claim 1, wherein a rotation of the actuator dial in a second rotational direction rotates the first roller in the second rotational direction.

5. The surgical device of claim 4, wherein the actuator dial has the shape of a disk, and a portion of the actuator dial extends through a slot formed on a sixth portion of the housing.

6. The surgical device of claim 1, wherein the distal end of the shaft is received into a first aperture formed in the first portion of the housing, the surgical device further comprising a channel that includes a first portion that includes the first aperture and a second portion that extends through a fifth portion of the housing, the channel extending along a channel axis that is coaxially aligned with the shaft axis, wherein the channel is configured to receive a first portion of a snare wire and the interior portion of the shaft is configured to receive a second portion of the snare wire, wherein the share wire is configured to contact a fourth portion of the suture to insert the second portion of the suture through the interior portion of the lumen when the first portion of the snare wire is removed from the proximal end of the channel.

7. The surgical device of claim 6, wherein the channel extends from a proximal end to a distal end along the channel axis, and the channel axis is coaxially aligned with the shaft axis.

8. The surgical device of claim 1, wherein the body axis of the distal tip body is coaxially aligned with the shaft axis.

9. The surgical device of claim 1, wherein the second roller is coupled to the first roller such that when the first roller rotates in the first rotational direction, the second roller rotates in a second rotational direction that is opposite to the first rotational direction, and when the actuator dial is rotated in the first rotational direction, the first roller and the second roller are configured to displace the lumen disposed between the first roller and the second roller in the first linear direction.

\* \* \* \* \*